United States Patent
Peters et al.

(10) Patent No.: US 7,959,986 B2
(45) Date of Patent: Jun. 14, 2011

(54) ORGANOMETALLIC COMPOUNDS, PROCESSES FOR THE PREPARATION THEREOF AND METHODS OF USE THEREOF

(75) Inventors: David Walter Peters, Kingsland, TX (US); David M. Thompson, East Amherst, NY (US)

(73) Assignee: Praxair Technology, Inc., Danbury, CT (US)

( * ) Notice: Subject to any disclaimer, the term of this patent is extended or adjusted under 35 U.S.C. 154(b) by 0 days.

(21) Appl. No.: 12/364,197

(22) Filed: Feb. 2, 2009

(65) Prior Publication Data

US 2009/0136684 A1 May 28, 2009

(51) Int. Cl.
*H05H 1/24* (2006.01)
(52) U.S. Cl. .................................. 427/576; 427/250
(58) Field of Classification Search .................. None
See application file for complete search history.

(56) References Cited

U.S. PATENT DOCUMENTS

| | | | |
|---|---|---|---|
| 3,288,829 A | 11/1966 | Wilkinson | |
| 3,437,516 A | 4/1969 | Tamborski | |
| 5,130,172 A | 7/1992 | Hicks et al. | |
| 5,668,054 A | 9/1997 | Sun et al. | |
| 5,789,027 A | 8/1998 | Watkins et al. | |
| 6,015,917 A | 1/2000 | Bhandare et al. | |
| 6,287,965 B1 | 9/2001 | Kang et al. | |
| 6,342,277 B1 | 1/2002 | Sherman | |
| 6,379,748 B1 | 4/2002 | Bhandari et al. | |
| 6,491,978 B1 * | 12/2002 | Kalyanam | 427/255.394 |
| 6,541,278 B2 | 4/2003 | Morita et al. | |
| 6,605,735 B2 | 8/2003 | Kawano et al. | |
| 6,743,473 B1 * | 6/2004 | Parkhe et al. | 427/252 |
| 6,884,901 B2 | 4/2005 | Thompson et al. | |
| 7,383,559 B2 | 6/2008 | Ohgi | |
| 2004/0142555 A1 * | 7/2004 | Kamepalli et al. | 438/643 |
| 2006/0121307 A1 | 6/2006 | Matsuzawa et al. | |
| 2006/0154482 A1 | 7/2006 | Kondoh et al. | |
| 2006/0216928 A1 | 9/2006 | Chung et al. | |

FOREIGN PATENT DOCUMENTS

| | | |
|---|---|---|
| GB | 976573 | 11/1964 |
| JP | 2005069726 | 3/2005 |

OTHER PUBLICATIONS

Atwood et al., "Novel Precursors for High K Dielectrics and Metal Electrodes Part II: Deposition", *Electrochemical Society Proceedings*, vol. 2003-08, pp. 847-854 (2003).

Bunker et al., "Mono-and Bis-η-cyclopentadienyl Derivatives of Niobium and Tantalum: Improved Synthetic Routes via Trialkyl (cyclopentadienyl)tin Reagents", *Journal of the Chemical Society,—Dalton*, 1980, 2155.

Camanyes et al., "Theoretical Study of the Hydroigen Exchange Coupling in the Metallocene Trihydride Complexes $[(C_5H_5)_2MH_3]^{n+}$ (M=Mo, W, n=1; M=Nb, Ta, n=0)" *Journal of the American Chemical Society*. XP-002427863. vol. 118, No. 19, 1996, pp. 4617-4621 (5 pgs).

Girling et al., "Vibrational Spectra of Terminal Metal Hydrides: Solution and Matrix-Isolation Studies of $[(\eta—C_5H_5)_2MH_\eta]^{x+}$ (M=Re, Mo, W, Nb, Ta; n=1-3; x=0, 1)" *Inorganic Chemistry*, XP-002427864, vol. 25, No. 1, pp. 31-36 (6 pgs.), 1986.

Green et al., "The Di-π-cyclopentadienyl Hydrides of Tantalum, Molybdenum, and Tungsten", *Journal of the Chemical Society—A*, 1961, 4854.

Legzdins et al., "Dicarbonyl($\eta^5$-Cyclopentadienyl)Nitrosyl Complexes of Chromium, Molybdenum, and Tungsten", *Inorg. Synth.*, 28, p. 196-198 (1990).

Lokshin et al., "Spectroscocpy of Unstable Complexes of Organometallic Compounds with Small Molecules at Low Temperatures" *Journal of Molecular Structure*, XP-002427865, vol. 222 (1990) pp. 11-20 (10 pgs).

Papke et al., "Evaluation of Metal-Organic Compounds as Materials for Chemical Vapor Deposition", *Proceedings of the Conference on CVD Refractory Metals*, 1975, 193-203.

Schrock et al., "Multiple Metal—Carbon Bonds. 7. Preparation and Characterization of $Ta(\eta^5-C_5H_5)_2(CH_2)$ ($CH_3$), a Study of Its Decomposition, and Some Simple Reactions" *Journal of the American Chemical Society* XP-0002427862. vol. 100, No. 8, 1978, pp. 1289-2399 (11 pgs).

Spee et al., "Tungsten Deposition by Organometallic Chemical Vapour Deposition with Organotungsten Precursors", *Materials Science and Engineering, B: Solid-State Materials for Advanced Technology*, XP-002427866, B17(1-3), pp. 108-111 (4 pgs.), 1993.

Stolz et al., "Universal Chemical Vapour Deposition System For Metallurgical Coatings", *Thin Solid Films*, 100, (1983) 209-218.

Zvukova et al., "Convenient Method of Synthesis of $Cp_2TaH_3$", *Russian Chemical Bulletin*, XP-002427861, vol. 44, No. 10, Oct. 1995, p. 1970 (1 pg.).

Zvukova et al., "Comparative Study of Methods for the Synthesis of Tantalocene Trihydride", *Metalloorganicheskaya Khimiya*, vol. 1, No. 5, pp. 1179-1183, 1988.

* cited by examiner

*Primary Examiner* — Timothy H Meeks
*Assistant Examiner* — Elizabeth Burkhart
(74) *Attorney, Agent, or Firm* — Iurie A. Schwartz

(57) ABSTRACT

This invention relates to organometallic precursor compounds represented by the formula $(Cp(R')_x)_yM(H)_{z-y}$, a process for producing the organometallic precursor compounds, and a method for depositing a metal and/or metal carbide layer, e.g., Ta metal and/or TaC layer, on a substrate by the thermal or plasma enhanced disassociation of the organometallic precursor compounds, e.g., by CVD or ALD techniques. The metal and/or metal carbide layer is useful as a liner or barrier layer for conducting metals and high dielectric constant materials in integrated circuit manufacturing.

14 Claims, No Drawings

ORGANOMETALLIC COMPOUNDS, PROCESSES FOR THE PREPARATION THEREOF AND METHODS OF USE THEREOF

CROSS-REFERENCE TO RELATED APPLICATION

The present invention claims priority to U.S. nonprovisional patent application Ser. No. 11/501,075 filed Aug. 9, 2006, now U.S. Pat. No. 7,547,796 B2, the contents of which are incorporated herein by reference in its entirety.

FIELD OF THE INVENTION

This invention relates to organometallic compounds, a process for producing organometallic compounds, and a method for producing a film or coating from organometallic precursor compounds.

BACKGROUND OF THE INVENTION

The semiconductor industry is currently considering the use of thin films of various metals for a variety of applications. Many organometallic complexes have been evaluated as potential precursors for the formation of these thin films. A need exists in the industry for developing new compounds and for exploring their potential as precursors for film depositions. The industry movement from physical vapor deposition (PVD) to chemical vapor deposition (CVD) and atomic layer deposition (ALD) processes, due to the increased demand for higher uniformity and conformality in thin films, has lead to a demand for suitable precursors for future semiconductor materials.

In the industry, conducting metals such as copper are being used to fill sub-micron features on substrates during the manufacture of integrated circuits. However, copper can diffuse into the structure of adjacent dielectric layers, thereby compromising the integrity of the devices being formed. Diffusion, as well as interlayer defects, such as layer delamination, may be prevented by depositing a barrier layer, a liner layer, or a combination of both, on the underlying material before depositing the conducting metal. The barrier layer is deposited on the underlying material and is often a nitride of a metal that prevents interlayer diffusion and minimizes chemical reactions between underlying materials and subsequently deposited materials. The liner layer is conventionally composed of a metal that provides adhesion for the conducting metal layer.

Metals such as tantalum, niobium, tungsten, and the respective metal nitrides are being considered for liner and barrier materials in copper applications. See, for example, U.S. Pat. Nos. 6,491,978 B1 and 6,379,748 B1. Depending on the application, a liner adhesion layer and/or a diffusion barrier layer may comprise a metal, such as tantalum, niobium, or tungsten, a metal nitride layer, such as tantalum nitride, niobium nitride layer, or tungsten nitride, a metal and metal nitride stack, or other combinations of diffusion barrier materials. Metal and metal nitride layers have been traditionally deposited by PVD techniques. However, traditional PVD techniques are not well suited for providing conformal coverage on the wall and bottom surfaces of high aspect ratio vias and other features. Therefore, as aspect ratios increase and device features shrink, new precursors and deposition techniques are being investigated to provide conformal coverage in these device features.

As referred to above, one proposed alternative to PVD techniques of metal and metal nitride layers is depositing the layers by CVD techniques to provide good conformal coverage of substrate features. The ability to deposit conformal metal and metal nitride layers in high aspect ratio features by the disassociation of organometallic precursors has gained interest in recent years due to the development of CVD techniques. In such techniques, an organometallic precursor comprising a metal component and organic component is introduced into a processing chamber and disassociates to deposit the metal component on a substrate while the organic portion of the precursor is exhausted from the chamber.

There are few commercially available organometallic precursors for the deposition of metal layers, such as tantalum, niobium, and tungsten precursors by CVD techniques. The precursors that are available produce layers which may have unacceptable levels of contaminants such as carbon and oxygen, and have less than desirable diffusion resistance, low thermal stability, and undesirable layer characteristics. Further, in some cases, the available precursors used to deposit metal nitride layers produce layers with high resistivity, and in some cases, produce layers that are insulative.

Another proposed alternative to PVD processes is ALD processes. ALD technology is considered superior to PVD technology in depositing thin films. However, the challenge for ALD technology is availability of suitable precursors. ALD deposition process involves a sequence of steps. The steps include 1) adsorption of precursors on the surface of substrate; 2) purging off excess precursor molecules in gas phase; 3) introducing reactants to react with precursor on the substrate surface; and 4) purging off excess reactant.

For ALD processes, the precursor should meet stringent requirements. First, the ALD precursors should be able to form a monolayer on the substrate surface either through physisorption or chemisorption under the deposition conditions. Second, the adsorbed precursor should be stable enough to prevent premature decomposition on the surface to result in high impurity levels. Third, the adsorbed molecule should be reactive enough to interact with reactants to leave a pure phase of the desirable material on the surface at relatively low temperature.

As with CVD, there are few commercially available organometallic precursors for the deposition of metal layers, such as tantalum, niobium, and tungsten precursors by ALD techniques. ALD precursors that are available may have one or more of following disadvantages: 1) low vapor pressure, 2) wrong phase of the deposited material, and 3) high carbon incorporation in the film.

Therefore, there remains a need for developing new compounds and for exploring their potential as CVD and ALD precursors for film depositions. There also remains a need for a process for forming liner and/or barrier layers of metal or metal derivative materials from organometallic precursors using CVD and ALD techniques. Ideally, the liner and/or barrier layers deposited are substantially free of contaminants, have reduced layer resistivities, improved interlayer adhesion, improved diffusion resistance, and improved thermal stability over those produced with PVD processes.

SUMMARY OF THE INVENTION

This invention relates to compounds having the formula $(Cp(R')_x)_y M(H)_{x-y}$, wherein M is a metal selected from tantalum (Ta), tungsten (W), molybdenum (Mo), niobium (Nb), vanadium (V) or chromium (Cr), each R' is the same or different and represents a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms, Cp is a substituted or unsubstituted cyclopentadienyl group or a substituted or unsubstituted cyclopentadienyl-like group, x is an integer from 0 to 5, y is an integer from 1 to 5, and z is the valence of M.

This invention relates to organometallic precursors having the formula $(Cp(R')_x)_yM(H)_{z-y}$ wherein M is a metal selected from tantalum (Ta), tungsten (W), molybdenum (Mo), niobium (Nb), vanadium (V) or chromium (Cr), each R' is the same or different and represents a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms, Cp is a substituted or unsubstituted cyclopentadienyl group or a substituted or unsubstituted cyclopentadienyl-like group, x is an integer from 0 to 5, y is an integer from 1 to 5, and z is the valence of M.

This invention relates to a process for producing a compound having the formula $(Cp(R')_x)_yM(H)_{z-y}$ wherein M is a metal selected from tantalum (Ta), tungsten (W), molybdenum (Mo), niobium (Nb), vanadium (V) or chromium (Cr), each R' is the same or different and represents a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms, Cp is a substituted or unsubstituted cyclopentadienyl group or a substituted or unsubstituted cyclopentadienyl-like group, x is an integer from 0 to 5, y is an integer from 1 to 5, and z is the valence of M, which process comprises reacting a metal halide, a cyclopentadienyl salt and a reducing agent in the presence of a first solvent and under reaction conditions sufficient to produce an intermediate reaction material, and reacting said intermediate reaction material with a base material in the presence of a second solvent and under reaction conditions sufficient to produce said compound.

This invention relates to a method for producing a film, coating or powder by decomposing an organometallic precursor, said organometallic precursor having the formula $(Cp(R')_x)_yM(H)_{z-y}$ wherein M is a metal selected from tantalum (Ta), tungsten (W), molybdenum (Mo), niobium (Nb), vanadium (V) or chromium (Cr), each R' is the same or different and represents a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms, Cp is a substituted or unsubstituted cyclopentadienyl group or a substituted or unsubstituted cyclopentadienyl-like group, x is an integer from 0 to 5, y is an integer from 1 to 5, and z is the valence of M, thereby producing said film, coating or powder.

This invention relates to a method for processing a substrate in a processing chamber, said method comprising (i) introducing an organometallic precursor into said processing chamber, said organometallic precursor having the formula $(Cp(R')_x)_yM(H)_{z-y}$ wherein M is a metal selected from tantalum (Ta), tungsten (W), molybdenum (Mo), niobium (Nb), vanadium (V) or chromium (Cr), each R' is the same or different and represents a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms, Cp is a substituted or unsubstituted cyclopentadienyl group or a substituted or unsubstituted cyclopentadienyl-like group, x is an integer from 0 to 5, y is an integer from 1 to 5, and z is the valence of M, (ii) heating said substrate to a temperature of about 100° C. to about 400° C., and (iii) disassociating said organometallic precursor in the presence of a processing gas to deposit a metal layer on said substrate.

DETAILED DESCRIPTION OF THE INVENTION

As indicated above, this invention relates to organometallic precursor compounds capable of forming metal-based materials, e.g., a metal and metal carbide such as Ta metal and TaC, W metal and WC, and Nb metal and NbC, on a substrate by techniques such as CVD and ALD. The substrate can preferably be microelectronic device structures for applications such as copper metallization of semiconductor device structures.

The organometallic precursor compounds of this invention useful for the formation of metal-based material layers, e.g., Ta metal and TaC barrier layers, include those compounds having the formula $(Cp(R')_x)_yM(H)_{z-y}$ wherein M is a metal selected from tantalum (Ta), tungsten (W), molybdenum (Mo), niobium (Nb), vanadium (V) or chromium (Cr), each R' is the same or different and represents a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms, Cp is a substituted or unsubstituted cyclopentadienyl group or a substituted or unsubstituted cyclopentadienyl-like group, x is an integer from 0 to 5, y is an integer from 1 to 5, and z is the valence of M.

This invention in part provides organometallic precursors and a method of processing a substrate to form a metal layer and/or metal carbide layer on the substrate by CVD or ALD of the organometallic precursor. The metal or metal carbide layer is deposited on a heated substrate by thermal or plasma enhanced disassociation of the organometallic precursor having the formula $(Cp(R')_x)_yM(H)_{z-y}$ in the presence of a processing gas. The processing gas may be an inert gas, such as helium and argon, and combinations thereof. The composition of the processing gas is selected to deposit metal and metal carbide layers as desired.

For the organometallic precursors of this invention represented by the formula $(Cp(R')_x)_yM(H)_{z-y}$, M represents the metal to be deposited. Examples of metals which can be deposited according to this invention are the Group VIB metals of tungsten, molybdenum and chromium, and the Group VB metals of vanadium, tantalum, and niobium. Y is the valence of the metal, M, of the precursor, with a valence of 6 for the Group VIB metals and a valence of 5 for the Group VB metals.

Cp is a cyclopentadienyl ring having the general formula $(C_5H_5-)$ which forms a ligand with the metal, M. The cyclopentadienyl ring may be substituted, thereby having the formula $(Cp(R')_x)_n$, where n is the number of cyclopentadienyl groups forming ligands with the metal, M. At least one, but generally between 1 and 5 cyclopentadienyl groups form a ligand with the metal, M, in forming the precursor. The precursor preferably contains two cyclopentadienyl groups.

Illustrative substituted cyclopentadienyl-like moieties include cyclo-olefin e.g., cyclohexadienyl, cycloheptadienyl, cyclooctadienyl rings, heterocyclic rings, aromatic rings, such as substituted benzenyl, and others, as known in the art.

Permissible substituents of the substituted cyclopentadienyl and cyclopentadienyl-like groups include halogen atoms, acyl groups having from 1 to about 12 carbon atoms, alkoxy groups having from 1 to about 12 carbon atoms, alkoxycarbonyl groups having from 1 to about 12 carbon atoms, alkyl groups having from 1 to about 12 carbon atoms, amine groups having from 1 to about 12 carbon atoms or silyl groups having from 0 to about 12 carbon atoms.

Illustrative halogen atoms include, for example, fluorine, chlorine, bromine and iodine. Preferred halogen atoms include chlorine and fluorine.

Illustrative acyl groups include, for example, formyl, acetyl, propionyl, butyryl, isobutyryl, valeryl, 1-methylpropylcarbonyl, isovaleryl, pentylcarbonyl, 1-methylbutylcarbonyl, 2-methylbutylcarbonyl, 3-methylbutylcarbonyl, 1-ethylpropylcarbonyl, 2-ethylpropylcarbonyl, and the like. Preferred acyl groups include formyl, acetyl and propionyl.

Illustrative alkoxy groups include, for example, methoxy, ethoxy, n-propoxy, isopropoxy, n-butoxy, isobutoxy, sec-butoxy, tert-butoxy, pentyloxy, 1-methylbutyloxy, 2-methylbutyloxy, 3-methylbutyloxy, 1,2-dimethylpropyloxy, hexyloxy, 1-methylpentyloxy, 1-ethylpropyloxy, 2-methylpentyloxy, 3-methylpentyloxy, 4-methylpentyloxy, 1,2-dimethylbutyloxy, 1,3-dimethylbutyloxy, 2,3-dimethylbutyloxy, 1,1-dimethylbutyloxy, 2,2-dimethylbutyloxy, 3,3-dimethylbutyloxy, and the like. Preferred alkoxy groups include methoxy, ethoxy and propoxy.

Illustrative alkoxycarbonyl groups include, for example, methoxycarbonyl, ethoxycarbonyl, propoxycarbonyl, isopropoxycarbonyl, cyclopropoxycarbonyl, butoxycarbonyl, isobutoxycarbonyl, sec-butoxycarbonyl, tert-butoxycarbonyl, and the like. Preferred alkoxycarbonyl groups include methoxycarbonyl, ethoxycarbonyl, propoxycarbonyl, isopropoxycarbonyl and cyclopropoxycarbonyl.

Illustrative alkyl groups include, for example, methyl, ethyl, n-propyl, isopropyl, n-butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, cyclopropyl, cyclobutyl, cyclopentyl, cyclohexyl, cyclopropylmethyl, cyclopropylethyl, cyclobutylmethyl, and the like. Preferred alkyl groups include methyl, ethyl, n-propyl, isopropyl and cyclopropyl.

Illustrative amine groups include, for example, methylamine, dimethylamine, ethylamine, diethylamine, propylamine, dipropylamine, isopropylamine, diisopropylamine, butylamine, dibutylamine, tert-butylamine, di(tert-butyl) amine, ethylmethylamine, butylmethylamine, cyclohexylamine, dicyclohexylamine, and the like. Preferred amine groups include dimethylamine, diethylamine and diisopropylamine.

Illustrative silyl groups include, for example, silyl, trimethylsilyl, triethylsilyl, tris(trimethylsilyl)methyl, trisilylmethyl, methylsilyl and the like. Preferred silyl groups include silyl, trimethylsilyl and triethylsilyl.

In a preferred embodiment, this invention relates in part to organometallic tantalum compounds represented by the formula

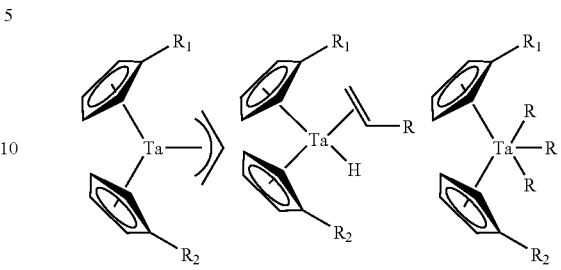

wherein $R_1$, $R_2$ and each R are the same or different and each represent a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms.

Illustrative organometallic compounds of this invention include, for example, bis(cyclopentadienyl)(allyl)tantalum, bis(cyclopentadienyl)(alkene)(hydrido)tantalum or bis(cyclopentadienyl)(trialkyl)tantalum, bis(cyclopentadienyl)(trihydrido)tantalum, and the like.

It is believed that the presence of the substituent groups on the cyclopentadienyl groups, particularly the silicon containing substituent groups, enhance preferred physical properties. It is believed that the substituent groups increase organometallic precursor volatility, decrease the temperature required to disassociate the precursor, and lower the boiling point of the organometallic precursor. An increased volatility of the organometallic precursor compounds ensures a sufficiently high concentration of precursor entrained in vaporized fluid flow to the processing chamber for effective deposition of a layer. The improved volatility will also allow the use of vaporization of the organometallic precursor by sublimation and delivery to a processing chamber without risk of premature disassociation. Additionally, the presence of substituent cyclopentadienyl groups may also provide sufficient solubility of the organometallic precursor for use in liquid delivery systems.

It is believed that the organometallic precursors described herein have functional groups which allow the formation of heat decomposable organometallic compounds that are thermally stable at temperatures below about 150° C. and are capable of thermally disassociating at a temperature above about 150° C. The organometallic precursors are also capable of disassociation in a plasma generated by supplying a power density at about 0.6 Watts/cm$^2$ or greater, or at about 200 Watts or greater for a 200 mm substrate, to a processing chamber.

The organometallic precursors described herein may deposit metal and metal carbide layers depending on the processing gas composition and the plasma gas composition for the deposition process. A metal or metal carbide layer is deposited in the presence of inert processing gases such as argon, a reactant processing gas, such as hydrogen, and combinations thereof.

It is believed that the use of a reactant processing gas, such as hydrogen, facilitates reaction with the cyclopentadienyl groups to form volatile gases, thereby removing the cyclopentadienyl ring from the precursor and depositing a metal or metal carbide layer on the substrate. The metal layer is preferably deposited in the presence of argon.

An exemplary processing regime for depositing a layer from the above described precursor is as follows. A precursor having the composition described herein, such as bis(cyclopentadienyl)(allyl)tantalum and a processing gas is introduced into a processing chamber. The precursor is introduced at a flow rate between about 5 and about 500 sccm and the processing gas is introduced into the chamber at a flow rate of between about 5 and about 500 sccm. In one embodiment of the deposition process, the precursor and processing gas are introduced at a molar ratio of about 1:1. The processing chamber is maintained at a pressure between about 100 milliTorr and about 20 Torr. The processing chamber is preferably maintained at a pressure between about 100 milliTorr and about 250 milliTorr. Flow rates and pressure conditions may vary for different makes, sizes, and models of the processing chambers used.

Thermal disassociation of the precursor involves heating the substrate to a temperature sufficiently high to cause the hydrocarbon portion of the volatile metal compound adjacent the substrate to disassociate to volatile hydrocarbons which desorb from the substrate while leaving the metal on the substrate. The exact temperature will depend upon the identity and chemical, thermal, and stability characteristics of the organometallic precursor and processing gases used under the deposition conditions. However, a temperature from about room temperature to about 400° C. is contemplated for the thermal disassociation of the precursor described herein.

The thermal disassociation is preferably performed by heating the substrate to a temperature between about 100° C. and about 400° C. In one embodiment of the thermal disassociation process, the substrate temperature is maintained between about 250° C. and about 450° C. to ensure a complete reaction between the precursor and the reacting gas on the substrate surface. In another embodiment, the substrate is maintained at a temperature below about 400° C. during the thermal disassociation process.

For plasma-enhanced CVD processes, power to generate a plasma is then either capacitively or inductively coupled into the chamber to enhance disassociation of the precursor and increase reaction with any reactant gases present to deposit a layer on the substrate. A power density between about 0.6 Watts/cm$^2$ and about 3.2 Watts/cm$^2$, or between about 200 and about 1000 Watts, with about 750 Watts most preferably used for a 200 mm substrate, is supplied to the chamber to generate the plasma.

After disassociation of the precursor and deposition of the material on the substrate, the deposited material may be exposed to a plasma treatment. The plasma comprises a reactant processing gas, such as hydrogen, an inert gas, such as argon, and combinations thereof. In the plasma-treatment process, power to generate a plasma is either capacitively or inductively coupled into the chamber to excite the processing gas into a plasma state to produce plasma specie, such as ions, which may react with the deposited material. The plasma is generated by supplying a power density between about 0.6 Watts/cm$^2$ and about 3.2 Watts/cm$^2$, or between about 200 and about 1000 Watts for a 200 mm substrate, to the processing chamber.

In one embodiment the plasma treatment comprises introducing a gas at a rate between about 5 sccm and about 300 sccm into a processing chamber and generating a plasma by providing a power density between about 0.6 Watts/cm$^2$ and about 3.2 Watts/cm$^2$, or a power at between about 200 Watts and about 1000 Watts for a 200 mm substrate, maintaining the chamber pressure between about 50 milliTorr and about 20 Torr, and maintaining the substrate at a temperature of between about 100° C. and about 400° C. during the plasma process.

It is believed that the plasma treatment lowers the layer's resistivity, removes contaminants, such as carbon or excess hydrogen, and densities the layer to enhance barrier and liner properties. It is believed that species from reactant gases, such as hydrogen species in the plasma react with the carbon impurities to produce volatile hydrocarbons that can easily desorb from the substrate surface and can be purged from the processing zone and processing chamber. Plasma species from inert gases, such as argon, further bombard the layer to remove resistive constituents to lower the layers resistivity and improve electrical conductivity.

Plasma treatments are preferably not performed for metal carbide layers, since the plasma treatment may remove the desired carbon content of the layer. If a plasma treatment for a metal carbide layer is performed, the plasma gases preferably comprise inert gases, such as argon and helium, to remove carbon.

It is believed that depositing layers from the above identified precursors and exposing the layers to a post deposition plasma process will produce a layer with improved material properties. The deposition and/or treatment of the materials described herein are believed to have improved diffusion resistance, improved interlayer adhesion, improved thermal stability, and improved interlayer bonding.

In an embodiment of this invention, a method for metallization of a feature on a substrate is provided that comprises depositing a dielectric layer on the substrate, etching a pattern into the substrate, depositing a metal carbide layer on the dielectric layer, and depositing a conductive metal layer on the metal carbide layer. The substrate may be optionally exposed to reactive pre-clean comprising a plasma of hydrogen and argon to remove oxide formations on the substrate prior to deposition of the metal carbide layer. The conductive metal is preferably copper and may be deposited by physical vapor deposition, chemical vapor deposition, or electrochemical deposition. The metal layer and the metal carbide layer are deposited by the thermal or plasma enhanced disassociation of an organometallic precursor of this invention in the presence of a processing gas, preferably at a pressure less than about 20 Torr. Once deposited, the metal layer and the metal carbide layer can be exposed to a plasma prior to subsequent layer deposition.

Current copper integration schemes involve a diffusion barrier with a copper wetting layer on top followed by a copper seed layer. A layer of TaC gradually becoming tantalum rich in accordance with this invention would replace multiple steps in the current integration schemes. The TaC layer is an excellent barrier to copper diffusion due to its amorphous character. The tantalum rich layer functions as a wetting layer and may allow for direct plating onto the tantalum. This single layer could be deposited in one step by manipulating the deposition parameters during the deposition. A post deposition treatment may also be employed to increase the ratio of tantalum in the film. Removal of one or more steps in semiconductor manufacture will result in substantial savings to the semiconductor manufacturer.

TaC films from $Cp_2TaH_3$ are deposited at temperatures lower than 400° C. and form no corrosive byproducts. TaC films are amorphous and are superior barriers than TaN to copper diffusion. By tuning the deposition parameters and post deposition treatment, the TaC barrier can have a tantalum rich film deposited on top of it. This tantalum rich film acts as a wetting layer for copper and may allow for direct copper plating on top of the Ta layer. In an embodiment, the deposition parameters may be tuned to provide a layer in which the composition varies across the thickness of the layer. For example, the layer may be TaC rich at the silicon portion surface of the microchip, e.g., good barrier properties, and Ta rich at the copper layer surface, e.g., good adhesive properties.

As also indicated above, this invention also relates in part to a process for producing the organometallic compound represented by the formula $(Cp(R')_x)_yM(H)_{z-y}$ wherein M is a metal selected from tantalum (Ta), tungsten (W), molybdenum (Mo), niobium (Nb), vanadium (V) or chromium (Cr), each R' is the same or different and represents a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, an amine group having from 1 to about 12 carbon atoms or a silyl group having from 0 to about 12 carbon atoms, Cp is a substituted or unsubstituted cyclopentadienyl group or a substituted or unsubstituted cyclopentadienyl-like group, x is an integer from 0 to 5, y is an integer from 1 to 5, and z is the valence of M, which process comprises reacting a metal halide, a cyclopentadienyl salt and a reducing agent in the presence of a first solvent and under reaction conditions sufficient to produce an intermediate reaction material, and reacting said intermediate reaction material with a base material in the presence of a second solvent and under reaction conditions sufficient to produce said organometallic precursors. The organometallic compound yield resulting from the process of this invention can be 40% or greater, preferably 35% or greater, and more preferably 30% or greater.

The process is particularly well-suited for large scale production since it can be conducted using the same equipment, some of the same reagents and process parameters that can easily be adapted to manufacture a wide range of products. The process provides for the synthesis of organometallic precursor compounds using a process where all manipulations can be carried out in a single vessel, and which route to the organometallic precursor compounds does not require the isolation of an intermediate complex.

The metal halide compound starting material may be selected from a wide variety of compounds known in the art. The invention herein most prefers metals selected from tantalum (Ta), tungsten (W), molybdenum (Mo), niobium (Nb), vanadium (V) or chromium (Cr). Illustrative metal halide compounds include, for example, tantalum pentachloride, niobium pentachloride, vanadium pentachloride, tungsten hexachloride, molybdenum hexachloride, chromium hexachloride, and the like.

The concentration of the metal source compound starting material can vary over a wide range, and need only be that minimum amount necessary to react with the cyclopentadienyl salt and reducing agent to produce the intermediate reaction material and to provide the given metal concentration desired to be employed and which will furnish the basis for at least the amount of metal necessary for the organometallic compounds of this invention. In general, depending on the size of the reaction mixture, metal source compound starting material concentrations in the range of from about 1 millimole or less to about 10,000 millimoles or greater, should be sufficient for most processes.

The cyclopentadienyl salt starting material may be selected from a wide variety of compounds known in the art. Illustrative cyclopentadienyl salts include sodium cyclopentadiene, potassium cyclopentadiene, lithium cyclopentadiene, magnesocene, and the like. The cyclopentadienyl salt starting material is preferably sodium cyclopentadiene and the like.

The concentration of the cyclopentadienyl salt starting material can vary over a wide range, and need only be that minimum amount necessary to react with the metal source compound starting material and reducing agent to produce an intermediate reaction material. In general, depending on the size of the first reaction mixture, cyclopentadienyl salt starting material concentrations in the range of from about 1 millimole or less to about 10,000 millimoles or greater, should be sufficient for most processes.

The reducing agent starting material may be selected from a wide variety of materials known in the art. Illustrative reducing agents include sodium bis(2-methoxyethoxy)aluminum dihydride (e.g., Red-Al® and Vitride reducing agent materials), sodium borohydride, lithium aluminum hydride, and the like. The reducing agent material is preferably sodium bis(2-methoxyethoxy)aluminum dihydride (e.g., Red-Al® reducing agent material), and the like.

The concentration of the reducing agent starting material can vary over a wide range, and need only be that minimum amount necessary to react with the metal source compound starting material and cyclopentadienyl salt starting material to produce an intermediate reaction material. In general, depending on the size of the first reaction mixture, reducing agent starting material concentrations in the range of from about 1 millimole or less to about 10,000 millimoles or greater, should be sufficient for most processes.

The first solvent employed in the method of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, silicone oils, other aprotic solvents, or mixtures of one or more of the above; more preferably, diethylether, pentanes, or dimethoxyethanes; and most preferably toluene or dimethoxyethane (DME) or mixtures thereof. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the cyclopentadienyl salt compound and reducing agent with the metal source compound to produce the intermediate reaction material, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 120° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

The intermediate reaction material may be selected from a wide variety of materials known in the art. Illustrative intermediate reaction materials include bis(cyclopentadienyl)(dihydrido)tantalum(bis-(2-methoxyethoxy)aluminate. The intermediate reaction material is preferably bis(cyclopentadienyl)(dihydrido)tantalum(bis-(2-methoxyethoxy)aluminate, and the like. The process of this invention does not require isolation of the intermediate reaction material.

The concentration of the intermediate reaction material can vary over a wide range, and need only be that minimum amount necessary to react with the base material to produce the organometallic compounds of this invention. In general, depending on the size of the second reaction mixture, intermediate reaction material concentrations in the range of from about 1 millimole or less to about 10,000 millimoles or greater, should be sufficient for most processes.

The base material may be selected from a wide variety of materials known in the art. Illustrative base materials include sodium hydroxide, potassium hydroxide, ethyl acetate, and the like. The base material is preferably sodium hydroxide and the like.

The concentration of the base material can vary over a wide range, and need only be that minimum amount necessary to react with the intermediate reaction material to produce the organometallic compounds of this invention. In general, depending on the size of the second reaction mixture, base material concentrations in the range of from about 1 millimole or less to about 10,000 millimoles or greater, should be sufficient for most processes.

The second solvent employed in the method of this invention may be any saturated and unsaturated hydrocarbons, aromatic hydrocarbons, aromatic heterocycles, alkyl halides, silylated hydrocarbons, ethers, polyethers, thioethers, esters, thioesters, lactones, amides, amines, polyamines, silicone oils, other aprotic solvents, or mixtures of one or more of the above; more preferably, diethylether, pentanes, or dimethoxyethanes; and most preferably toluene, hexane mixtures thereof. Any suitable solvent which does not unduly adversely interfere with the intended reaction can be employed. Mixtures of one or more different solvents may be employed if desired. The amount of solvent employed is not critical to the subject invention and need only be that amount sufficient to solubilize the reaction components in the reaction mixture. In general, the amount of solvent may range from about 5 percent by weight up to about 99 percent by weight or more based on the total weight of the reaction mixture starting materials.

Reaction conditions for the reaction of the intermediate reaction material with the base material to produce the organometallic precursors of this invention, such as temperature, pressure and contact time, may also vary greatly and any suitable combination of such conditions may be employed herein. The reaction temperature may be the reflux temperature of any of the aforementioned solvents, and more preferably between about −80° C. to about 150° C., and most preferably between about 20° C. to about 120° C. Normally the reaction is carried out under ambient pressure and the contact time may vary from a matter of seconds or minutes to a few hours or greater. The reactants can be added to the reaction mixture or combined in any order. The stir time employed can range from about 0.1 to about 400 hours, preferably from about 1 to 75 hours, and more preferably from about 4 to 16 hours, for all steps.

Other alternative processes that may be used in preparing the organometallic compounds of this invention include those disclosed in U.S. Pat. No. 6,605,735 B2 and U.S. Patent Application Publication No. US 2004/0127732 A1, published Jul. 1, 2004, the disclosure of which is incorporated herein by reference. The organometallic compounds of this invention may also be prepared by conventional processes such as described in Legzdins, P. et al. Inorg. Synth. 1990, 28, 196 and references therein.

For organometallic compounds prepared by the method of this invention, purification can occur through recrystallization, more preferably through extraction of reaction residue (e.g., hexane) and chromatography, and most preferably through sublimation and distillation.

Those skilled in the art will recognize that numerous changes may be made to the method described in detail herein, without departing in scope or spirit from the present invention as more particularly defined in the claims below.

Examples of techniques that can be employed to characterize the organometallic compounds formed by the synthetic methods described above include, but are not limited to, analytical gas chromatography, nuclear magnetic resonance, thermogravimetric analysis, inductively coupled plasma mass spectrometry, differential scanning calorimetry, vapor pressure and viscosity measurements.

Relative vapor pressures, or relative volatility, of organometallic compound precursors described above can be measured by thermogravimetric analysis techniques known in the art. Equilibrium vapor pressures also can be measured, for example by evacuating all gases from a sealed vessel, after which vapors of the compounds are introduced to the vessel and the pressure is measured as known in the art.

The organometallic compound precursors described herein are well suited for preparing in-situ powders and coatings. For instance, an organometallic compound precursor can be applied to a substrate and then heated to a temperature sufficient to decompose the precursor, thereby forming a metal or metal carbide, e.g., Ta metal or TaC, coating on the substrate. Applying the precursor to the substrate can be by painting, spraying, dipping or by other techniques known in the art. Heating can be conducted in an oven, with a heat gun, by electrically heating the substrate, or by other means, as known in the art. A layered coating can be obtained by applying an organometallic compound precursor, and heating and decomposing it, thereby forming a first layer, followed by at least one other coating with the same or different precursors, and heating.

Organometallic compound precursors such as described above also can be atomized and sprayed onto a substrate. Atomization and spraying means, such as nozzles, nebulizers and others, that can be employed are known in the art.

This invention provides in part an organometallic precursor and a method of forming a metal or metal carbide layer on a substrate by CVD or ALD of the organometallic precursor. In one aspect of the invention, an organometallic precursor of this invention is used to deposit a metal or metal carbide layer at subatmospheric pressures. The method for depositing the metal or metal carbide layer comprises introducing the precursor into a processing chamber, preferably maintained at a pressure of less than about 20 Torr, and disassociating the precursor in the presence of a processing gas to deposit a metal or metal carbide layer. The precursor may be disassociated and deposited by a thermal or plasma-enhanced process. The method may further comprise a step of exposing the deposited layer to a plasma process to remove contaminants, densify the layer, and reduce the layer's resistivity.

In preferred embodiments of the invention, an organometallic compound, such as described above, is employed in gas phase deposition techniques for forming powders, films or coatings. The compound can be employed as a single source precursor or can be used together with one or more other precursors, for instance, with vapor generated by heating at least one other organometallic compound or metal complex. More than one organometallic compound precursor, such as described above, also can be employed in a given process.

As indicated above, this invention also relates in part to a method for producing a film, coating or powder. The method includes the step of decomposing at least one organometallic compound precursor, thereby producing the film, coating or powder, as further described below.

Deposition methods described herein can be conducted to form a film, powder or coating that includes a single metal or a film, powder or coating that includes a single metal or metal carbide, e.g., Ta metal or TaC. Mixed films, powders or coatings also can be deposited, for instance mixed metal/metal carbide films.

Gas phase film deposition can be conducted to form film layers of a desired thickness, for example, in the range of from about 1 nm to over 1 mm. The precursors described herein are particularly useful for producing thin films, e.g., films having a thickness in the range of from about 10 nm to about 100 nm. Films of this invention, for instance, can be considered for fabricating metal electrodes, in particular as n-channel metal electrodes in logic, as capacitor electrodes for DRAM applications, and as dielectric materials.

The method also is suited for preparing layered films, wherein at least two of the layers differ in phase or composition. Examples of layered film include metal-insulator-semiconductor, and metal-insulator-metal.

In an embodiment, the invention is directed to a method that includes the step of decomposing vapor of an organometallic compound precursor described above, thermally, chemically, photochemically or by plasma activation, thereby forming a film on a substrate. For instance, vapor generated by the compound is contacted with a substrate having a temperature sufficient to cause the organometallic compound to decompose and form a film on the substrate.

The organometallic compound precursors can be employed in chemical vapor deposition or, more specifically, in metal organic chemical vapor deposition processes known in the art. For instance, the organometallic compound precursors described above can be used in atmospheric, as well as in low pressure, chemical vapor deposition processes. The compounds can be employed in hot wall chemical vapor deposition, a method in which the entire reaction chamber is heated, as well as in cold or warm wall type chemical vapor deposition, a technique in which only the substrate is being heated.

The organometallic compound precursors described above also can be used in plasma or photo-assisted chemical vapor deposition processes, in which the energy from a plasma or electromagnetic energy, respectively, is used to activate the chemical vapor deposition precursor. The compounds also can be employed in ion-beam, electron-beam assisted chemical vapor deposition processes in which, respectively, an ion beam or electron beam is directed to the substrate to supply energy for decomposing a chemical vapor deposition precursor. Laser-assisted chemical vapor deposition processes, in which laser light is directed to the substrate to affect photolytic reactions of the chemical vapor deposition precursor, also can be used.

The method of the invention can be conducted in various chemical vapor deposition reactors, such as, for instance, hot or cold-wall reactors, plasma-assisted, beam-assisted or laser-assisted reactors, as known in the art.

Examples of substrates that can be coated employing the method of the invention include solid substrates such as metal substrates, e.g., Al, Ni, Ti, Co, Pt, metal silicides, e.g., $TiSi_2$, $CoSi_2$, $NiSi_2$; semiconductor materials, e.g., Si, SiGe, GaAs, InP, diamond, GaN, SiC; insulators, e.g., $SiO_2$, $Si_3N_4$, $HfO_2$, $Ta_2O_5$, $Al_2O_3$, barium strontium titanate (BST); or on substrates that include combinations of materials. In addition, films or coatings can be formed on glass, ceramics, plastics, thermoset polymeric materials, and on other coatings or film layers. In preferred embodiments, film deposition is on a substrate used in the manufacture or processing of electronic components. In other embodiments, a substrate is employed to support a low resistivity conductor deposit that is stable in the presence of an oxidizer at high temperature or an optically transmitting film.

The method of this invention can be conducted to deposit a film on a substrate that has a smooth, flat surface. In an embodiment, the method is conducted to deposit a film on a substrate used in wafer manufacturing or processing. For instance, the method can be conducted to deposit a film on patterned substrates that include features such as trenches, holes or vias. Furthermore, the method of the invention also can be integrated with other steps in wafer manufacturing or processing, e.g., masking, etching and others.

In an embodiment of this invention, a plasma assisted ALD (PEALD) method has been developed for using the organometallic precursors to deposit TaC and tantalum rich films. The solid precursor can be sublimed under the flow of an inert gas to introduce it into a CVD chamber. TaC films are grown on a substrate with the aid of a hydrogen plasma. The ratio of tantalum to carbon can be controlled by controlling the pulse duration of the hydrogen plasma.

Chemical vapor deposition films can be deposited to a desired thickness. For example, films formed can be less than 1 micron thick, preferably less than 500 nanometers and more preferably less than 200 nanometers thick. Films that are less than 50 nanometers thick, for instance, films that have a thickness between about 0.1 and about 20 nanometers, also can be produced.

Organometallic compound precursors described above also can be employed in the method of the invention to form films by ALD processes or atomic layer nucleation (ALN) techniques, during which a substrate is exposed to alternate pulses of precursor, oxidizer and inert gas streams. Sequential layer deposition techniques are described, for example, in U.S. Pat. No. 6,287,965 and in U.S. Pat. No. 6,342,277. The disclosures of both patents are incorporated herein by reference in their entirety.

For example, in one ALD cycle, a substrate is exposed, in step-wise manner, to: a) an inert gas; b) inert gas carrying precursor vapor; c) inert gas; and d) oxidizer, alone or together with inert gas. In general, each step can be as short as the equipment will permit (e.g. milliseconds) and as long as the process requires (e.g. several seconds or minutes). The duration of one cycle can be as short as milliseconds and as long as minutes. The cycle is repeated over a period that can range from a few minutes to hours. Film produced can be a few nanometers thin or thicker, e.g., 1 millimeter (mm).

This invention includes a method for forming a metal material, e.g., Ta metal or TaC, on a substrate, e.g., a microelectronic device structure, from an organometallic precursor of this invention, said method comprising vaporizing said organometallic precursor to form a vapor, and contacting the vapor with the substrate to form said metal material thereon. After Ta metal or TaC is deposited on the substrate, the substrate may thereafter be metallized with copper or integrated with a ferroelectric thin film.

The method of the invention also can be conducted using supercritical fluids. Examples of film deposition methods that use supercritical fluid that are currently known in the art include chemical fluid deposition; supercritical fluid transport-chemical deposition; supercritical fluid chemical deposition; and supercritical immersion deposition.

Chemical fluid deposition processes, for example, are well suited for producing high purity films and for covering complex surfaces and filling of high-aspect-ratio features. Chemical fluid deposition is described, for instance, in U.S. Pat. No. 5,789,027. The use of supercritical fluids to form films also is described in U.S. Pat. No. 6,541,278 B2. The disclosures of these two patents are incorporated herein by reference in their entirety.

In an embodiment of the invention, a heated patterned substrate is exposed to one or more organometallic compound precursors, in the presence of a solvent, such as a near critical or supercritical fluid, e.g., near critical or supercritical $CO_2$. In the case of $CO_2$, the solvent fluid is provided at a pressure above about 1000 psig and a temperature of at least about 30° C.

The precursor is decomposed to form a metal film on the substrate. The reaction also generates organic material from the precursor. The organic material is solubilized by the solvent fluid and easily removed away from the substrate.

In an example, the deposition process is conducted in a reaction chamber that houses one or more substrates. The substrates are heated to the desired temperature by heating the entire chamber, for instance, by means of a furnace. Vapor of the organometallic compound can be produced, for example, by applying a vacuum to the chamber. For low boiling compounds, the chamber can be hot enough to cause vaporization of the compound. As the vapor contacts the heated substrate surface, it decomposes and forms a metal or metal carbide film. As described above, an organometallic compound precursor can be used alone or in combination with one or more components, such as, for example, other organometallic precursors, inert carrier gases or reactive gases.

In a system that can be used in producing films by the method of the invention, raw materials can be directed to a gas-blending manifold to produce process gas that is supplied to a deposition reactor, where film growth is conducted. Raw materials include, but are not limited to, carrier gases, reactive gases, purge gases, precursor, etch/clean gases, and others. Precise control of the process gas composition is accomplished using mass-flow controllers, valves, pressure transducers, and other means, as known in the art. An exhaust manifold can convey gas exiting the deposition reactor, as well as a bypass stream, to a vacuum pump. An abatement system, downstream of the vacuum pump, can be used to remove any hazardous materials from the exhaust gas. The deposition system can be equipped with in-situ analysis system, including a residual gas analyzer, which permits measurement of the process gas composition. A control and data acquisition system can monitor the various process parameters (e.g., temperature, pressure, flow rate, etc.).

The organometallic compound precursors described above can be employed to produce films that include a single metal or a film that includes a single metal carbide. Mixed films also can be deposited, for instance mixed metal carbide films. Such films are produced, for example, by employing several organometallic precursors. Metal films also can be formed, for example, by using no carrier gas, vapor or other sources of oxygen.

Films formed by the methods described herein can be characterized by techniques known in the art, for instance, by X-ray diffraction, Auger spectroscopy, X-ray photoelectron emission spectroscopy, atomic force microscopy, scanning electron microscopy, and other techniques known in the art. Resistivity and thermal stability of the films also can be measured, by methods known in the art.

In addition to their use in semiconductor applications as chemical vapor or atomic layer deposition precursors for film depositions, the organometallic compounds of this invention may also be useful, for example, as catalysts, fuel additives and in organic syntheses.

Various modifications and variations of this invention will be obvious to a worker skilled in the art and it is to be understood that such modifications and variations are to be included within the purview of this application and the spirit and scope of the claims.

Example 1

The thin film deposition system used in this example is described in detail in J. Atwood, D. C. Hoth, D. A. Moreno, C. A. Hoover, S. H. Meiere, D. M. Thompson, G. B. Piotrowski, M. M. Litwin, J. Peck, *Electrochemical Society Proceedings* 2003-08, (2003) 847. $Cp_2TaH_3$ was sublimed at 90° C. using 100 sccm of argon in a flow cell vaporizer at 50 Torr. The precursor/argon mixture was combined with additional argon to form the process gas mixture. Thin films were generated using a pulsed process, consisting of 4 steps. The substrate (typically 3 inch $SiO_2$ wafer) was exposed to the process gas mixture at 5 Torr and from 350 to 450° C. In step 1, the process gas mixture contained the precursor ($Cp_2TaH_3$). After exposing the substrate to the mixture of precursor and argon for a specified period of time (typically 10 seconds), the flow of precursor was interrupted and the reactor was purged using argon. The purge step (step 2) was typically conducted for 20 seconds. During step 3 (typically 10 seconds), the substrate was exposed to a mixture of hydrogen and argon, in the presence of a plasma discharge. The plasma was generated using a capacitively coupled RF configuration. Between 20 and 160 Watts of forward power was applied to generate the plasma. In step 4 (typically 20 seconds), the reactor was again purged with argon. This pulsed process was repeated until the desired thickness of Ta containing film was deposited.

A silicon dioxide wafer was used as the substrate at 362° C. A plasma enhanced ALD (PEALD) process with timing of 10/20/10/20 seconds was repeated for 50 cycles to grow a tantalum containing film that measured four nanometers by elipsometry. Thicker films can be grown by increasing the number of cycles.

Example 2

In order to prevent THF from reacting with the tantalum complex, sodium cyclopentadiene (NaCp) was first synthesized via a THF free route. A slight excess of freshly cracked cyclopentadiene dimer was reacted with sodium bistrimethylsilylamide in ether.

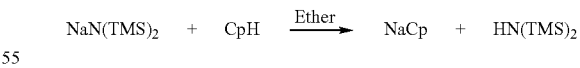

The solid product was purified by filtration and rinsing with ether. 1 equivalent of tantalum pentachloride ($TaCl_5$) was added to a solution of three equivalents of NaCp and three equivalents of the reducing agent Vitride® (commercially available from Sigma Aldrich) in dimethoxy ethane (DME). The solution was heated to reflux for four hours and then the solvent was replaced with toluene.

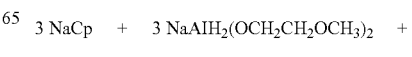

-continued

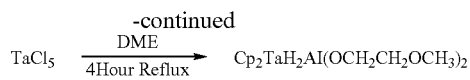

The reaction was cooled to 0° C. and one equivalent of distilled, degassed water was added. This is followed by one equivalent of 15% sodium hydroxide solution and three equivalents of water.

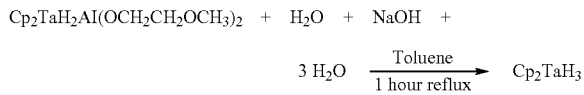

The reaction was then heated to reflux for an hour and allowed to cool. The reaction mixture was filtered through a pad of magnesium sulfate to remove excess water and the solvent was removed under reduced pressure. The solid was washed two to three times with pentane to yield a slightly off white solid. The solid was characterized by NMR in $C_6D_6$. We observed a single peak at 4.8 for the Cp resonance and a triplet and a doublet at 1.6 and 2.9 for the hydride resonances. At this point, sublimation can be performed at 100° C. and $10^{-2}$ torr for further purification. Further purification is not necessary for the deposition method described above as the chemical delivery is a sublimation.

The invention claimed is:

1. A method for producing a film, coating or powder by decomposing an organometallic precursor, said organometallic precursor having the formula

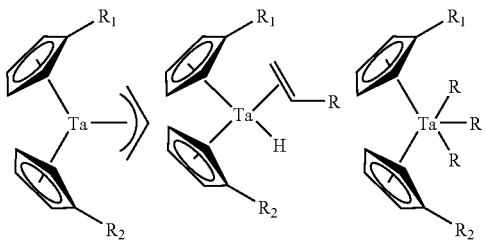

wherein $R_1$, $R_2$ and each R are the same or different and each represent a halogen atom, an acyl group having from 1 to about 12 carbon atoms, an alkoxy group having from 1 to about 12 carbon atoms, an alkoxycarbonyl group having from 1 to about 12 carbon atoms or an amine group having from 1 to about 12 carbon atoms, thereby producing said film, coating or powder.

2. The method of claim 1 wherein the decomposing of said organometallic precursor is thermal, chemical, photochemical or plasma-activated.

3. The method of claim 1 wherein said organometallic precursor is vaporized and the vapor is directed into a deposition reactor housing a substrate.

4. The method of claim 3 wherein said substrate is comprised of a material selected from the group consisting of a metal, a metal silicide, a semiconductor, an insulator and a barrier material.

5. The method of claim 3 wherein said organometallic precursor is deposited on said substrate by chemical vapor deposition, atomic layer deposition, plasma assisted chemical vapor deposition or plasma assisted atomic layer deposition.

6. The method of claim 3 wherein Ta or TaC is deposited on said substrate.

7. A method for forming a metal material on a substrate from an organometallic precursor, said method comprising vaporizing said organometallic precursor to form a vapor, and contacting the vapor with the substrate to form said metal material thereon, wherein the substrate comprises a microelectronic device structure, and wherein the precursor is represented by the formula

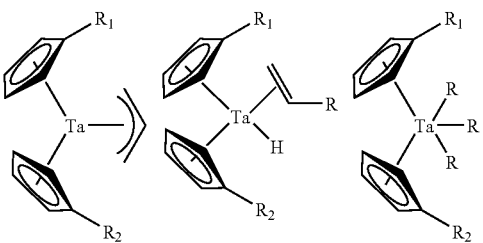

wherein $R_1$, $R_2$ and each R are the same or different and each represent a halogen atom, an acyl group having from 1 to about 12 carbon atoms, an alkoxy group having from 1 to about 12 carbon atoms, an alkoxycarbonyl group having from 1 to about 12 carbon atoms, or an amine group having from 1 to about 12 carbon atoms.

8. The method of claim 7 wherein the metal material comprises Ta metal or TaC.

9. The method of claim 7 wherein Ta metal or TaC is deposited on said substrate, and the substrate is thereafter metallized with copper or integrated with a ferroelectric thin film.

10. A method of fabricating a microelectronic device structure, said method comprising vaporizing an organometallic precursor having the formula

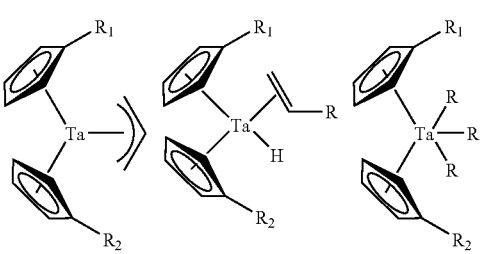

wherein $R_1$, $R_2$ and each R are the same or different and each represent a halogen atom, an acyl group having from 1 to about 12 carbon atoms, an alkoxy group having from 1 to about 12 carbon atoms, an alkoxycarbonyl group having from 1 to about 12 carbon atoms, or an amine group having from 1 to about 12 carbon atoms, to form a vapor, an contacting said vapor with a substrate to deposit a metal-containing film on the substrate, and thereafter metallizing the substrate with copper or integrating it with a ferroelectric thin film.

11. The method of claim 10 wherein the metal-containing film comprises Ta metal or TaC.

12. A method for producing a film, coating or powder by decomposing an organometallic precursor, said organometallic precursor having the formula

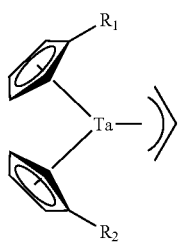 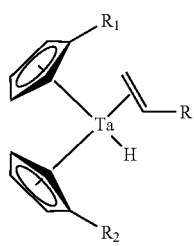

wherein $R_1$, $R_2$ and each R are the same or different and each represent a hydrogen atom, a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, or an amine group having from 1 to about 12 carbon atoms, thereby producing said film, coating or powder.

13. A method for forming a metal material on a substrate from an organometallic precursor, said method comprising vaporizing said organometallic precursor to form a vapor, and contacting the vapor with the substrate to form said metal material thereon, wherein the substrate comprises a microelectronic device structure, and wherein the precursor is represented by the formula

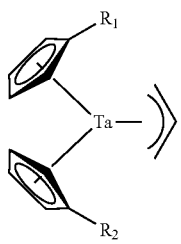 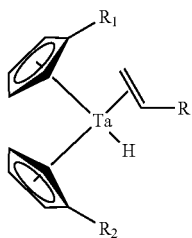

wherein $R_1$, $R_2$ and each R are the same or different and each represent a hydrogen atom, a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, or an amine group having from 1 to about 12 carbon atoms.

14. A method of fabricating a microelectronic device structure, said method comprising vaporizing an organometallic precursor having the formula

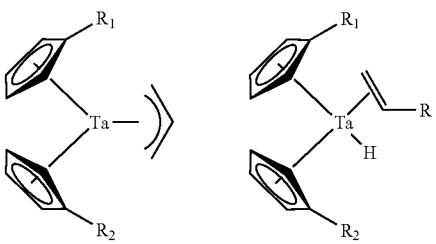

wherein $R_1$, $R_2$ and each R are the same or different and each represent a hydrogen atom, a halogen atom, an acyl group having from 1 to about 12 carbon atoms, an alkoxy group having from 1 to about 12 carbon atoms, an alkoxycarbonyl group having from 1 to about 12 carbon atoms, an alkyl group having from 1 to about 12 carbon atoms, or an amine group having from 1 to about 12 carbon atoms, to form a vapor, an contacting said vapor with a substrate to deposit a metal-containing film on the substrate, and thereafter metallizing the substrate with copper or integrating it with a ferroelectric thin film.

* * * * *